United States Patent [19]

Arnott

[11] Patent Number: 4,701,181

[45] Date of Patent: Oct. 20, 1987

[54] POSTERIOR CHAMBER LENS IMPLANT

[76] Inventor: Eric J. Arnott, 75 Abbotsbury Road, London W14, England

[21] Appl. No.: 881,084

[22] Filed: Jul. 2, 1986

[51] Int. Cl.⁴ .............................................. A61F 2/16
[52] U.S. Cl. .................................................. 623/6
[58] Field of Search ......................................... 623/6

[56] References Cited

U.S. PATENT DOCUMENTS 4,476,591 10/1984 Arnott ..................................... 623/6

OTHER PUBLICATIONS

The Jaffe Single Piece Posterior Chamber Lens from Cilco JF1LRU, Advertisement Cilco, Inc., 2 pages, Oct. 1984.
"Kamerling Capsular 90" Model No. 6200 (Advertisement Sheet), Precision-Cosmet Company, Inc., 11140 Bren Road West, Minnetonka, MN 55343, 1985.
"Clayman 7MM Ovoid One-Piece" Model No. 5770 & 5772UV, (Advertisment Sheet), Precision-Cosmet Company, Inc., Minnetonka, MN, 1985.

Primary Examiner—Ronald L. Frinks
Attorney, Agent, or Firm—Brumbaugh, Graves Donohue & Raymond

[57] ABSTRACT

A posterior chamber lens implant has a lens and a pair of haptics or holding loops. Each loop has an elongated flange projecting from the lens and extending approximately one-quarter of the way around the lens periphery. A free loop portion projects from the flange and curves around the lens so as to overlap the flange of the other loop. Accordingly, the flanges are positioned, relative to the loops, so as to be substantially axially oriented during implantation and so that one flange acts as an insertion guide for the lens body. When implanted, the loops encircle the lens so as to center the lens and protect the lens against secondary fiber growth.

4 Claims, 3 Drawing Figures

POSTERIOR CHAMBER LENS IMPLANT

The present invention relates to posterior chamber lens implants for insertion in the human eye from which the natural lens has been removed by an extra-capsular extraction. More specifically, the novel lens implant disclosed herein constitutes an improvement over the lens implant disclosed in my U.S. Pat. No. 4,476,591 letter.

BACKGROUND OF THE INVENTION

Posterior chamber lens implants consist of a lens, typically made of polymethylmethacrylate (PMMA), and haptic portions projecting from the lens periphery. The haptic portions hold the lens in position in the eye, within the capsular bag between the posterior capsule and the iris, after the implant has been inserted through an incision at the junction of the cornea and the sclera. The haptics are in the form of closed loops or curved arms, which lie generally in the plane of the lens.

During implantation, a posterior chamber lens is inserted into the posterior chamber through the pupil. In order to pass through the pupil, the loops must be compressed, since the pupil cross-section is relatively narrow. Once the implant is in the larger, posterior chamber, it is necessary that the loops spring open again so as to press outwardly against the interior of the posterior chamber to seat and hold the lens insert in place.

Because posterior chamber implants require such highly flexible loops, in the past the loops for such implants were made of Prolene rather than PMMA. Prolene loops can be made relatively thin and highly flexible and resilient to facilitate insertion through the pupil. Moreover, Prolene loops, when implanted, do not press with excessive force against the interior surface of the eye. However, Prolene is subject to degradation in the eye, so attempts were made to use PMMA loops. Because of the relative properties of PMMA, the substitution of PMMA resulted in loops which were too stiff, and thus unable to bend sufficiently, or which exerted excessive outward force, or which, if made too thin, were subject to breaking.

My U.S. Pat. No. 4,476,591 discloses a lens implant with holding loops or arms having a geometry in which the loops are made of PMMA but are nevertheless highly flexible and, when implanted, hold the lens without exerting excessive force against the interior surface of the eye. According to this lens design, the loops project radially outwardly from the lens, and then bend sharply and extend around the lens a distance so as to overlap one another, i.e. to encircle the lens. Not only does this lens possess highly flexible loops, but the fact that the loops completely encircle the lens enhances the centering properties of the loops and forms a protective barrier to inhibit the growth of secondary fibers inwardly over the posterior capsule.

In the '591 implant, each loop includes a first portion that extends substantially radially outwards from the lens, a sharp bend, a second loop portion with a curvature that follows the lens circumference, a third loop portion that extends from the second loop portion and has a curvature less than the immediately preceding loop portion, and a fourth loop portion that extends from the third loop portion and has a greater curvature than the third loop portion, e.g. substantially similar to that of the second portion. In this manner, the loops, when compressed toward one another, as occurs when the lens is implanted in the eye, maintain their encircling configuration and bend into a more circular shape. The encircling loops provide a large contact area between the loops and the interior surface of the eye to distribute the holding force over a greater area. Also, since secondary fibers tend eventually to grow around the loops and hold them in place, the larger contact area promotes long term stability of the lens in the eye.

Another advantage of this lens configuration occurs during insertion of the lens. Posterior chamber lenses are implanted by forming an incision in the cornea and inserting the lens axially through the incision. When the lens is oriented for insertion, the stiff first loop portions are substantially axially aligned, i.e. project axially rather than laterally from the lens proper. This means that a smaller incision may be used.

Because the end of each loop overlaps the other loop, care must be taken, when compressing the loops during implantation, to ensure that the free end of one loop does not become entangled with the other loop. If this were to occur, it would be necessary to free the caught end so that the loops could spring outwardly and engage the inner circumferential walls of the capsular bag into which the lens is implanted. It would, however, be desirable to eliminate this possible complication while retaining the substantial benefits of my prior lens insert.

SUMMARY OF THE INVENTION

The present invention is an improvement of the posterior chamber lens implant disclosed in U.S. Pat. No. 4,476,591, which retains the favorable characteristics of my prior lens but which incorporates an improved loop structure in the area of the first and second loop portions.

More particularly, I have modified my prior lens design so that the first loop portion is elongated circumferentially so as to extend along part of what was the second loop portion and thereby become an elongated flange. Because eye surgery is by nature very delicate, this modification in structure, which is discussed further below, provides significant advantages in implantation surgery.

A posterior chamber lens implant according to the invention includes a lens with a pair of similar holding loops formed integrally therewith. Each loop comprises a first flange portion projecting radially outwardly from the periphery of the lens proper. The flange has an outer edge subtending an arc that follows, but is spaced radially outwardly from, the periphery of the lens. Preferably, the flange portion extends around approximately one-quarter of the periphery of the lens. The loop also has a free, relatively thin loop portion projecting from the flange portion.

The flange portions of the two holding loops are substantially diametrically opposite each other around the periphery of the lens and the free loop portion of each loop curves around the lens so as to overlap the flange portion of the other loop. The free end of each loop, when the loop is compressed, contacts the flange portion, rather than the free loop portion, of the other loop.

The loops include a leading edge for insertion axially through an incision in the eye, and the opposed flange portions are substantially axially oriented along the direction of insertion, such that the forward flange portion (i.e. the flange that enters the incision first) acts as a guide for the lens during insertion. When implanted, the loops encircle the lens for centering the lens and for protecting the lens against secondary fiber growth.

In a preferred embodiment, the first, flange portion of the loop terminates at a relatively sharp bend at which juncture the free loop portion projects. The free loop portion includes a second loop portion extending from the bend. The curvature of the second loop portion follows, but is spaced radially outwards from the periphery of the lens body. A third loop portion extends from the second loop portion and has a curvature less than the second loop portion, and a fourth loop portion extends from the third loop portion and has a curvature greater than the third portion. The curvature of the fourth loop portion may be similar to the second loop portion. The end of the fourth loop portion is free and lies radially outwards of the elongated flange or first portion of the other loop.

In a lens implant according to the invention, the loops are normally compressed during implantation, and once the implant is properly in place, the loops partially spring open again to engage the fornix area of the lens capsule. The holding loops according to the invention are extremely flexible, which means they can be readily compressed during implantation, and will spring open without imparting excessive force on the fornix area. Moreover, when the free loop portions are compressed toward the lens body, the holding loops assume a more circular shape. Thus, the loops encircle the lens body and, when implanted in the eye, provide a relatively large substantially circular contact area for engaging the interior of the eye.

As noted above in the present invention I have elongated the outwardly projecting flange of the first loop portion, such that it extends partially along what was the second loop portion in U.S. Pat. No. 4,476,591. I have determined that providing a larger flange area in what was part of the second loop portion will not adversely affect the flexibility characteristics of the loop, since in practice the substantial flexure of the holding loops in the '591 patent occurs predominantly further outwardly of the second loop portion. Moreover, by modifying my prior lens so, the resultant lens is significantly improved.

First, the loops may be compressed toward one another to touch or even overlap, without concern about the free loop ends catching on the other loop during implantation. Second, when the lens is inserted through an incision in the cornea, the flange provides a large, uniform, flat surface, with a rounded leading edge portion, which is axially oriented relative to the direction of implant movement to assist in guiding the lens body through the incision. Third, in the construction according with the invention, less of the loop is free, and therefore there is less length of loop exposed to breaking off during handling, the free end of the loop being the most vulnerable part of the lens. Thus, a lens in accordance with this invention provides significant advantages in implementation procedure, and yet retains the flexibility characteristics of the loops disclosed in my U.S. Pat. No. 4,476,591.

The two loops or arms of the lens implant preferably lie in a flat plane, i.e. the plane of the lens. However, the loops may be constructed so as to lie in planes which are inclined to the plane of the lens by a small angle, e.g. 10°.

Preferably, each loop has rectangular cross-section and constant thickness, perpendicular to the plane of the lens. The first loop portion is of greater width in this plane than the other loop portions in order to provide stiffness. The width of the first loop portion tapers at its distal end to form the beginning of the second loop portion which in turn tapers slightly at its distal end to form the third loop portion. The third portion and the major part of the fourth portion are then preferably of constant width.

The width of the fourth portion of each loop is preferably increased at its free end. The widened free end of each loop and the first loop portions are preferably provided with positioning holes extending through them perpendicular to the plane of the lens. These positioning holes, when engaged by a suitable medical instrument, assist in moving the lens into the exact required position after it has been inserted.

An example of a lens implant in accordance with the invention is illustrated in the accompanying drawings and described in the accompanying detailed description.

DETAILED DESCRIPTION OF A PREFERRED EMBODIMENT

Figure 1:
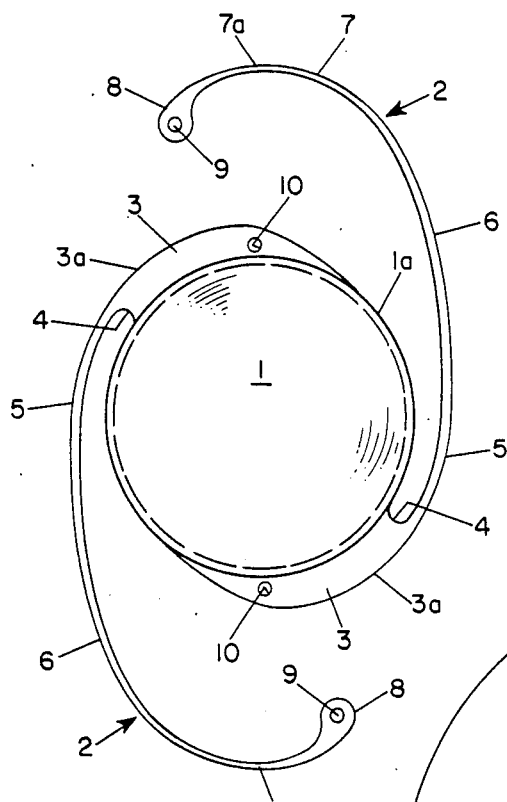
FIG. 1 is a front elevation of the implant.

The novel lens implant comprises a lens 1 and two holding loops 2 which are formed integrally with the lens 1. Each of the loops 2 has a first, flange portion 3 which projects substantially radially from the periphery 1a of lens 1 and is of substantial width so that it is relatively stiff against bending in the plane of lens 1. The flange portion 3 of each loop 2 has an outer edge 3a subtending an arc that follows, but is spaced radially outwards from, the lens periphery 1. As shown in FIG. 1, the flange 3 preferably extends around approximately one-quarter of the periphery of lens 1 and is connected around a sharp bend 4 to a narrower second loop portion 5 which projects along the arc of the outer edge 3a and has a curvature such that it is substantially concentric with the periphery 1a of lens 1. A third narrow loop portion 6 extends from loop portion 5 and has a curvature substantially less than that of loop portion 5. A fourth narrow loop portion 7 extends from the third loop portion 6, and has a curvature similar to the second loop portion 5.

Each loop, taken as a whole, is approximately symmetrical about an axis lying substantially in the plane of lens 1 and perpendicular to the center of the third loop portion 6. The free end of each loop, i.e. the end of the fourth loop portion 7, is formed with a widened tip member 8 and a positioning hole 9 formed therein. Each loop is further formed with a second positioning hole 10 formed near the proximal end of the flange portion 3.

As can be seen easily from FIG. 1, flange portions 3 of the loops 2 are positioned substantially diametrically opposite each other around the periphery of the lens 1 and therefore the loops 2, which are substantially identical, are symmetrically disposed around the lens.

The portions 5, 6 and 7 are sufficiently flexible and resilient so that when loops 2 are bent in the plane of the lens, with loop portions 7 being pushed towards the periphery of lens 1, the tip 8 of one loop will come into contact with flange portion 3 of the other loop. The loops are squeezed inwardly to enable the lens implant as a whole to be inserted into the posterior chamber of the eye in front of the posterior capsule.

Figure 2:
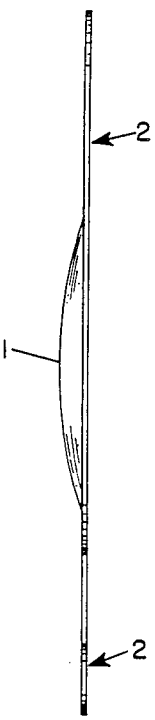
FIG. 2 is a side elevation as seen from the lefthand side of FIG. 1.

Lens 1, which is plano-convex as can be seen from FIG. 2, has, by way of example, a diameter of 5.5 mm. Flanges 3 are flat, and the free loop portions 5, 6, and 7 may be flat or inclined relative to the plane of the lens by a small angle, e.g. 10°. By way of further example, both loops 2 and have a constant thickness of 0.14 mm perpendicular to the plane of the lens. Loop portion 5 has a width of 0.22 mm adjacent its junction with loop portion 3 and the width tapers uniformly to 0.17 mm at the junction between loop portions 5 and 6. Loop portions 6 and 7 have a constant width of 0.17 mm up to the widened top 8. The positioning holes 9 have a diameter of 0.4 mm. The height of the lens implant as oriented in FIG. 1, is 13.5 mm and the width is 8.0 mm.

Figure 3:
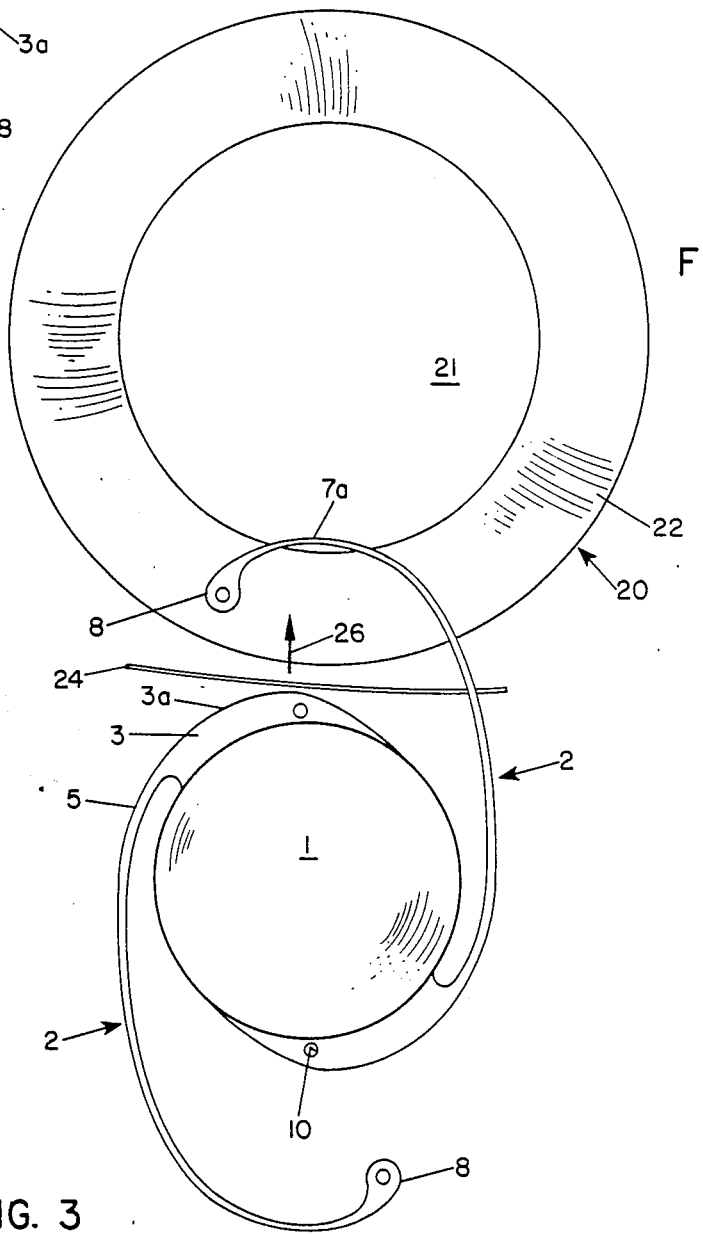
FIG. 3 is a schematic view of a lens according to the invention illustrating an implantation procedure.

FIG. 3 shows schematically a portion of an eye 20 including a pupil 21. A posterior chamber lens is implanted by first making an incision 24 in the cornea and removing the natural lens by an extra-capsular extraction. The lens implant is then inserted through the incision 24. The lens is oriented so that the leading edge 7a of one of the loops enters the incision first and the lens body 1 thereafter slides axially through the incision as shown by arrow 26. Forceps and other known medical instruments are used for this procedure.

As can be seen from FIG. 3, when the lens body 1 enters the incision 24, the flat flange 3 enters first. The flange 3 presents a relatively large, rounded leading edge, i.e. edge 3a, which acts as an insertion guide for the lens. Moreover, when the lens 1 enters the incision, stiff flange 3 enters first rather than the thin, and relatively weak, free loop portion, e.g. 5. As can also be seen in FIG. 3, as the lens moves through incision 24, the flanges 3 are substantially axially oriented. If desired, the loop portions 5 can be compressed toward the lens body 1 so as to reduce the width of the implant during insertion (thereby reducing the size of the necessary incision 24).

The leading loop and lens body 1 are directed to extend through the pupil 21 so as to be behind the iris and inferior anterior capsular flap 22. Thereafter the loops 2 are compressed so as to position the second (or trailing) loop behind the anterior capsular flap iris. This may be done by dialing the lens, using hole 10, or by looping the second lens. Using either technique, the tip 8 of each loop moves toward the other loop and may contact it or even overlap it during insertion. Once the lens is in place, the loops spring outwardly, but are more compressed than is shown in FIGS. 1 and 3, and therefore in a somewhat more circular configuration as they continue to encircle lens body 1.

As noted above, the elongated flange 3 extends along a portion of the loop 2 that does not tend to bend when the loops are compressed. Accordingly, this lens retains the favorable flexibility characteristics of the lens shown in the '591 patent. At the same time, the resultant novel lens provides significant advantages when used in the delicate operating procedures required by this type of microsurgery.

The foregoing is a preferred embodiment of the invention. Variations and modifications will be apparent to persons skilled in the art without departing from the inventive concepts disclosed herein. All such modifications and variations are intended to be within the scope of the invention, a set forth in the following claims.

I claim:

1. A posterior chamber lens implant comprising a lens having a periphery and a pair of similar holding loops formed integrally therewith, wherein each loop comprises a first flange portion projecting radially outwardly from said periphery and elongated circumferentially along said periphery, said flange portion having an outer edge subtending an arc spaced radially outwards from said periphery, and each loop further comprises a free, relatively thin loop portion projecting from said flange portion; wherein the flange portions of the holding loops are substantially diametrically opposite each other around the periphery of the lens; wherein the free loop portion of each loop is curved so as to overlap the flange portion of the other loop such that the loops encircle the lens; wherein the free loop portion, when compressed, contacts the flange portion, rather than the free loop portion, of the other loop; wherein the loops include a leading edge for insertion axially through an incision in the eye and the opposed flange portions are substantially axially oriented during such insertion such that one of the flange portions acts as a guide for the lens; and wherein the encircling loops, when implanted in the eye, act to center the lens and protect the lens against secondary fiber growth.

2. A lens implant as defined in claim 1, wherein the flange portion of each loop extends around approximately one-quarter of the lens periphery.

3. A lens implant as defined in claim 2, wherein said arc follows said periphery.

4. A lens implant as defined in claim 2, wherein the free loop portion includes a second loop portion connected around a sharp bend to the flange portion, the second loop portion projecting from said flange portion substantially along said arc and having a curvature that follows, but is spaced radially from, the lens periphery, a third loop portion projecting from the second loop portion and having less curvature than the second loop portion, and a fourth loop portion projecting from the third loop portion and having greater curvature than the third loop portion, the distal end of the fourth portion of each loop lying radially outward of the flange portion of the other loop.

* * * * *